United States Patent [19]

Hill et al.

[11] 4,115,642

[45] Sep. 19, 1978

[54] METHOD FOR PREPARING AURANOFIN

[75] Inventors: David T. Hill, North Wales, Pa.; Ivan Lantos, Blackwood, N.J.; Blaine M. Sutton, Hatboro, Pa.

[73] Assignee: SmithKline Corporation, Philadelphia, Pa.

[21] Appl. No.: 811,641

[22] Filed: Jun. 30, 1977

[51] Int. Cl.$^2$ ............................................. C07H 23/00
[52] U.S. Cl. ........................................ 536/121; 536/4; 536/122
[58] Field of Search ................................... 536/121, 4

[56] References Cited

U.S. PATENT DOCUMENTS 3,635,945   1/1972   Nemeth et al. .......................... 536/4

OTHER PUBLICATIONS

Sutton et al., J. Med. Chem. 15, 1095 (1972).

Primary Examiner—Johnnie R. Brown
Assistant Examiner—Blondel Hazel
Attorney, Agent, or Firm—William H. Edgerton

[57] ABSTRACT

Auranofin and its congeners are prepared by reacting a bis(polyacetylsaccharide)disulfide with a tertiary phosphinegold mercaptide in a suitable organic solvent.

5 Claims, No Drawings

METHOD FOR PREPARING AURANOFIN

This invention comprises a new synthetic method for preparing the antiarthritic agent, auranofin, and its congeners which uses a bis(polyacetylsaccharide)disulfide plus a mercaptide compound containing the group $(C_2H_5)_3$PAu-which is capable of entering a bimolecular displacement with the disulfide.

Auranofin has been demonstrated to be a useful oral antiarthritic agent in man [J. Med. Chem. 15, 1095 (1972); U.S. Pat. No. 3,635,945]. In these prior art references auranofin is prepared by the reaction of an alkali metal salt of a 1-thio-β-D-glucopyranose with a phosphinegold halide. That reaction is quite distinct from the invention disclosed hereafter.

The method of this invention may be illustrated by the following:

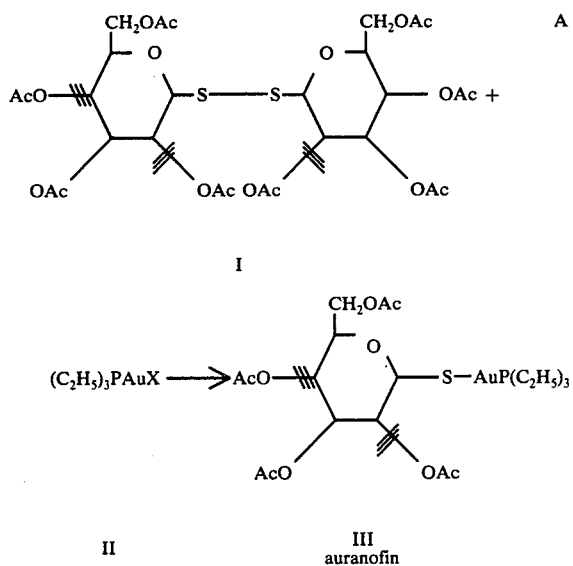

In this reaction, as known to the art Ac is acetyl. X is lower alkylthio of 1–6 carbon atoms for example methylthio, ethylthio or allylthio, aralkylthio such as benzylthio or phenethylthio or triethylphosphinegoldthio.

The starting materials for the method of this invention are either known or are prepared by synthetic routes similar to those in the art. For example the tertiaryphosphinegold mercaptides (II) are prepared by reaction of the phosphinegold bromide or chloride in chloroform-ethanol with the thiol in the presence of one mold equivalent of base, see G. E. Coates et al. Aust. J. Chem. 19, 536 (1966). The saccharride disulfide (I) is also prepared by known methods, see Whistler, Methods in Carbohydrate Chemistry, Academic Press, Vol. 2, 436 (1963).

The reaction described above is carried out by reacting equimolar quantities of the bis-saccharide disulfide (I) and the appropriate tertiaryphosphinegold mercaptide (II) in a solvent in which the reactants are soluble and to which they are inert such as a common halogenated hydrocarbon solvent such as chloroform, carbon tetrachloride, ethylene tetrachloride or methylene chloride, a benzenoid solvent such as benzene, toluene or xylene, dimethylformamide, dimethylacetamide, ethereal solvents such as diethylether or dioxane, ethyl acetate, ethyl carbonate, dimethyl sulfoxide or lower alkanols such as methanol, ethanol or isopropanol.

The reaction is allowed to continue until complete at from room temperature to the boiling point of the solvent. the time of the reaction depends on the conditions. However, it has been found that it is convenient to dissolve the reactants in a suitable solvent such as chloroform or methylene chloride and allow the mixture to stand at room temperature for from overnight to 3–4 days.

The desired product, for example auranofin, is isolated by standard isolation techniques. Such as evaporation of the solvent and purification of the reaction product mixture by chromatography of fractional crystallization.

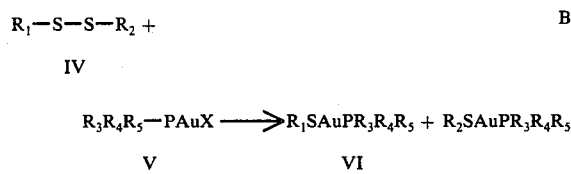

It will be noted that the bissaccharide disulfide (IV) can be varied widely but if the reaction is used to prepare auranofin one half of the disulfide must be the 2,3,4,6-tetra-O-acetyl-1-thio-β-D-glucopyranose radical. The other half of the disulfide ($R_2$) may be varied widely to include alkyl, aryl, or aralkyl groups. Mixtures of products would be obtained, therefore the symmetrical disulfides are preferred.

Also as noted above X can also vary widely to include any organic radical whose mercaptan derivative is readily prepared such as alkylthio, arylthio or aralkylthio moieties. The tertiary phosphine ligand of the reactant V may also vary widely to include those compounds known to serve as such ligands in which $R_3$, $R_4$ and $R_5$ may be alkyl or aryl. Of course for auranofin $R_3$, $R_4$ and $R_5$ need be ethyl.

Finally other O-functional derivatives of the glucopyranose radical can be used such as lower ethers such as methyl or ethyl, other acyls such as other lower alkanoyls.

The following examples are designed for illustration of the reactions of this invention. All temperatures are Centigrade.

EXAMPLE 1

A chloroform solution (30 ml) of 1.0 g (2.8 mmoles) of methylthio(triethylphosphine) gold and 2.0 g (2.8 mmoles) of bis(2,3,4,6-tetra-O-acetyl-β-D-glucopyranosyl)disulfide was stirred at room temperature for 48 hours. After filtration, the solvent was removed in vacuo and the colorless oil treated with 1.0 ml of methanol. The resultant solid was removed and dried to give 2.2 g of material which was treated with 15 ml of hot methanol, filtered and diluted with 10 ml of water to give 1.1 g of starting disulfide. An additional 10 ml of water was added to the mother liquors and the crystals which formed were removed by filtration, dissolved in benzene (3 ml), filtered and the solvent removed in vacuo. Recrystallization of the residue gave 0.38 g (20%) of auranofin, m.p. 104°–107°; $[\alpha]_D^{25}$ (1% methanol) = −58.7°.

The reaction may also be run at the reflux temperature of the reaction mixture to decrease reaction time and to obtain a more efficient conversion of disulfide starting material.

Other mercaptides such as ethylthio(triethylphosphine)gold, propylthio(triethylphosphine)gold, n-butylthio(triethylphosphine)gold, i-butylthio(triethylphosphine)gold and benzylthio(triethylphosphine)gold [G. E. Coates et al., Aust. J. Chem. 19, 539 (1966)] as well as their triphenylphosphine congeners [C. Kowala et al., Aust. J. Chem. 19, 547 (1966)] may be substituted in equimolar quantities for the mercaptide in the above reaction.

EXAMPLE 2

A chloroform solution (25 ml) of 1.0 g (1.5 mmole) of bis[(triethylhosphine) aurous] sulfide [Aust. J. Chem. 19, 522 (1966)] and 1.1 g (1.5 mmoles) of bis(2,3,4,6-tetra-O-acetyl-β-D-glucopyranosyl)disulfide was stirred overnight at room temperature, filtered and the solvent removed at reduced pressure. The residue was then chromatographed over silica gel using solvent gradient elution (benzene to chloroform). Chloroform (100%) elution gave a colorless oil which was crystallized from methanol-water to give auranofin, m.p. 106°–109°.

What is claimed is:

1. The method of preparing auranofin comprising reacting the compound of the formula:

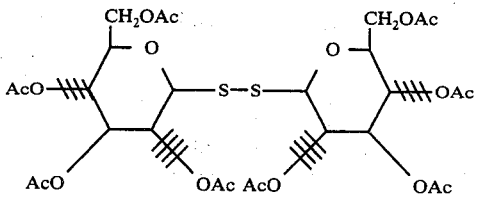

in which Ac is acetyl, with a compound of the formula:

$(C_2H_5)_3PAuX$ in which X is lower alkylthio of 1–6 carbons, benzylthio, phenethylthio or triethylphosphinegoldthio in an organic solvent in which said reactants are soluble and which is chemically inert toward the reactants.

2. The reaction of claim 1 in which the solvent is methylene chloride at temperatures from about room temperature up to the boiling point of the reaction mixture.

3. The reaction of claim 1 in which X is methylthio.

4. The reaction of claim 1 in which X is triethylphosphinegoldthio.

5. The reaction of claim 1 in which X is benzylthio.

* * * * *